United States Patent
Scheller et al.

(10) Patent No.: US 9,138,346 B2
(45) Date of Patent: Sep. 22, 2015

(54) SURGICAL INSTRUMENT SLEEVE

(75) Inventors: Gregg D. Scheller, Wildwood, MO (US); Craig Moore, O'Fallon, MO (US); Matthew N. Zeid, Ballwin, MO (US)

(73) Assignee: Katalyst Surgical, LLC, Chesterfield, MO (US)

( * ) Notice: Subject to any disclaimer, the term of this patent is extended or adjusted under 35 U.S.C. 154(b) by 225 days.

(21) Appl. No.: 13/602,028

(22) Filed: Aug. 31, 2012

(65) Prior Publication Data

US 2013/0197488 A1    Aug. 1, 2013

Related U.S. Application Data

(60) Provisional application No. 61/590,944, filed on Jan. 26, 2012.

(51) Int. Cl.
| | | |
|---|---|---|
| *A61B 17/00* | (2006.01) | |
| *A61F 9/007* | (2006.01) | |
| *A61B 17/34* | (2006.01) | |
| *A61B 17/30* | (2006.01) | |
| *A61B 19/00* | (2006.01) | |

(52) U.S. Cl.
CPC ......... *A61F 9/00736* (2013.01); *A61B 17/3496* (2013.01); *A61B 2017/305* (2013.01); *A61B 2019/481* (2013.01); *A61B 2019/4805* (2013.01); *A61F 9/007* (2013.01)

(58) Field of Classification Search
CPC ..................... A61B 17/3496; A61B 2017/305; A61B 2019/4805; A61B 2019/481; A61F 9/00736; A61F 9/007

USPC ............................................................ 606/1
See application file for complete search history.

(56) References Cited

U.S. PATENT DOCUMENTS

| | | | | |
|---|---|---|---|---|
| 3,659,607 | A * | 5/1972 | Banko ........................... | 606/169 |
| 5,190,050 | A * | 3/1993 | Nitzsche ....................... | 600/585 |
| 5,415,645 | A * | 5/1995 | Friend et al. .................. | 604/110 |
| 5,425,730 | A * | 6/1995 | Luloh .............................. | 606/15 |
| 6,551,291 | B1 * | 4/2003 | de Juan et al. ................ | 604/294 |
| 6,749,601 | B2 * | 6/2004 | Chin ................................ | 606/1 |
| 7,338,494 | B2 * | 3/2008 | Ryan .............................. | 606/79 |
| 7,783,346 | B2 * | 8/2010 | Smith et al. .................... | 604/21 |
| 7,935,080 | B2 * | 5/2011 | Howell et al. ................. | 604/110 |
| 2008/0255526 | A1 * | 10/2008 | Bosse et al. ................... | 604/263 |
| 2009/0131870 | A1 * | 5/2009 | Fiser .............................. | 604/162 |
| 2010/0063359 | A1 * | 3/2010 | Okoniewski .................. | 600/121 |
| 2010/0228226 | A1 * | 9/2010 | Nielsen ......................... | 604/506 |

* cited by examiner

*Primary Examiner* — Gary Jackson
*Assistant Examiner* — Scott T Luan
(74) *Attorney, Agent, or Firm* — Kevin P. Rollins

(57) ABSTRACT

A surgical instrument may have a handle, a support sleeve, and an inner sleeve. Illustratively, the support sleeve may be configured to actuate relative to the inner sleeve to protect the inner sleeve before and after a surgical procedure and to expose a portion of the inner sleeve during the surgical procedure. In one or more embodiments, an application of a force to a distal end of the support sleeve may be configured to retract the support sleeve relative to the inner sleeve. Illustratively, a reduction of a force applied to the distal end of the support sleeve may be configured to extend the support sleeve relative to the inner sleeve.

18 Claims, 11 Drawing Sheets

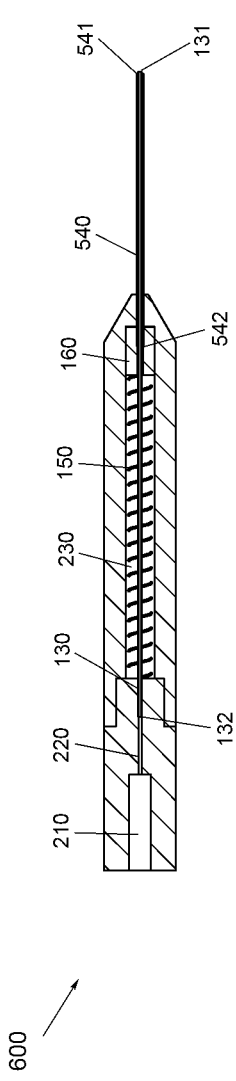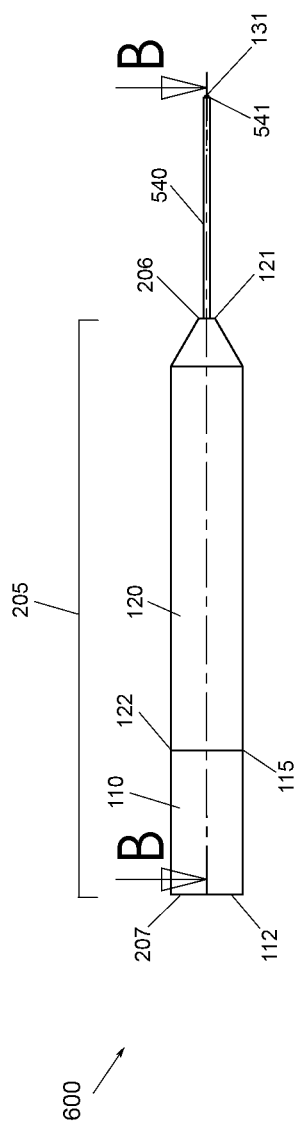
FIG. 6B
FIG. 6A

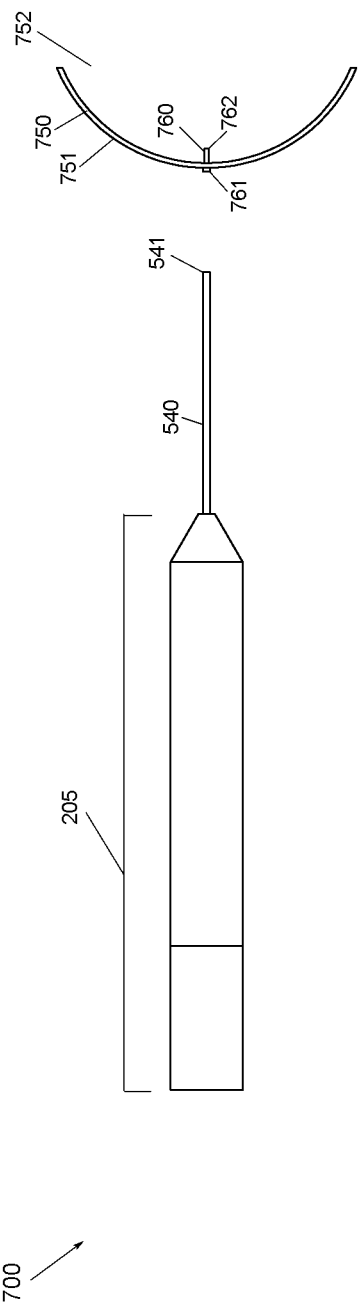

SURGICAL INSTRUMENT SLEEVE

CROSS-REFERENCE TO RELATED APPLICATIONS

This Application claims the benefit of U.S. Provisional Application No. 61/590944, filed Jan. 26, 2012.

FIELD OF THE INVENTION

The present disclosure relates to a surgical instrument, and, more particularly, to a surgical instrument sleeve.

BACKGROUND OF THE INVENTION

A variety of surgical procedures are performed with delicate surgical instruments that may be easily damaged even if the instruments are handled in a reasonable manner. Surgical instruments with dimensions configured for microsurgical procedures are particularly susceptible to damage because microsurgical instruments are typically designed and manufactured to provide surgical utility rather than instrument durability. For example, microsurgical instrument tips may be bent or broken with very little force. Even if a microsurgical instrument tip is not bent or broken, routine handling of an instrument may fatigue delicate portions of the instrument making the instrument unfit for use in a surgical procedure. Accordingly, there is a need for a mechanism to protect delicate portions of surgical instruments before and after surgical procedures.

In addition to being particularly susceptible to damage during routine handling, microsurgical instrument tips may actuate in unexpected directions if the instrument tips are inserted in a cannula. For example, during some ophthalmologic surgical procedures a cannula is inserted into an incision in the cornea or the sclera allowing a surgeon to access a surgical site within the inner eye, e.g., by inserting microsurgical instrument tips into the cannula. Once a microsurgical instrument tip is inserted in a cannula, a surgeon may attempt to direct a distal end of the microsurgical instrument tip towards a surgical target site, e.g., by manipulating a handle of the microsurgical instrument. Typically, a surgeon expects an instrument tip to actuate in a linear fashion with an instrument handle. For example, actuating the instrument handle in a direction, e.g., right, should actuate the instrument tip in the same plane but in the opposite direction, e.g., left, when the instrument tip is inserted in a cannula. However, some microsurgical instrument tips, e.g., 25 gauge instrument tips, are not easily actuated within a cannula because the instrument tips are too flexible. If a surgeon attempts to direct the distal end of a flexible microsurgical instrument tip towards a surgical site, e.g., by actuating the instrument handle right, then a portion of the cannula may act as a fulcrum causing the flexible instrument tip to actuate in an unexpected direction, e.g., right. Accordingly, there is a need for a mechanism to increase the stiffness of microsurgical instrument tips.

BRIEF SUMMARY OF THE INVENTION

The present disclosure provides a surgical instrument. In one or more embodiments, a surgical instrument may comprise a handle, a protective sleeve, and an inner sleeve. Illustratively, the protective sleeve may be configured to actuate relative to the inner sleeve to protect the inner sleeve before and after a surgical procedure and to expose a portion of the inner sleeve during the surgical procedure. In one or more embodiments, an application of a force to a distal end of the protective sleeve may be configured to retract the protective sleeve relative to the inner sleeve. Illustratively, a reduction of a force applied to the distal end of the protective sleeve may be configured to extend the protective sleeve relative to the inner sleeve.

In one or more embodiments, a surgical instrument may comprise a handle, a support sleeve, and an inner sleeve. Illustratively, the support sleeve may be configured to increase a stiffness of a portion of the inner sleeve. In one or more embodiments, the support sleeve may be configured to enclose a portion of the inner sleeve to prevent the inner sleeve from actuating in an unexpected direction when inserted in a cannula. Illustratively, the support sleeve may be configured to cause a distal end of the inner sleeve to actuate in a clockwise direction, e.g., in response to an actuation of the handle in a clockwise direction. In one or more embodiments, the support sleeve may be configured to prevent a distal end of the inner sleeve from actuating in a counter-clockwise direction, e.g., in response to an actuation of the handle in a clockwise direction. Illustratively, the support sleeve may be configured to cause a distal end of the inner sleeve to actuate in a counter-clockwise direction, e.g., in response to an actuation of the handle in a counter-clockwise direction. In one or more embodiments, the support sleeve may be configured to prevent a distal end of the inner sleeve from actuating in a clockwise direction, e.g., in response to an actuation of the handle in a counter-clockwise direction.

BRIEF DESCRIPTION OF THE DRAWINGS

The above and further advantages of the present invention may be better understood by referring to the following description in conjunction with the accompanying drawings in which like reference numerals indicate identical or functionally similar elements:

FIGS. 6A and 6B are schematic diagrams illustrating a surgical instrument;

FIGS. 7A, 7B, 7C, 7D, and 7E are schematic diagrams illustrating a surgical procedure with a surgical instrument.

DETAILED DESCRIPTION OF AN ILLUSTRATIVE EMBODIMENT

Figure 1:
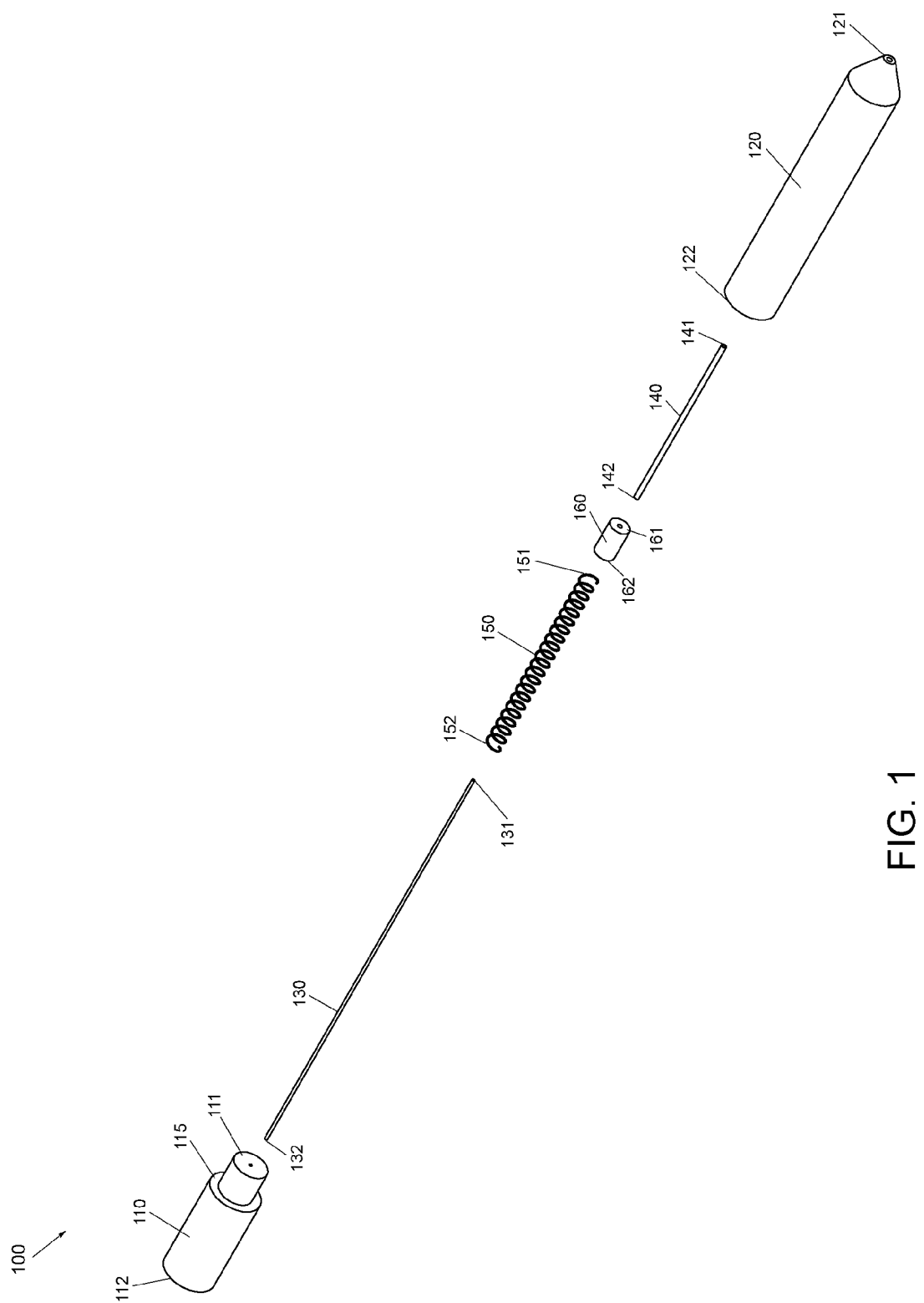
FIG. 1 is a schematic diagram illustrating an exploded view of a surgical instrument assembly.

FIG. 1 is a schematic diagram illustrating an exploded view of a surgical instrument assembly 100. In one or more embodiments, a surgical instrument assembly 100 may comprise a handle base component 110 having a handle base component distal end 111 and a handle base component proximal end 112, a handle base 120 having a handle base distal end 121 and a handle base proximal end 122, an inner sleeve 130 having an inner sleeve distal end 131 and an inner sleeve proximal end 132, a protective sleeve 140 having a protective sleeve distal end 141 and a protective sleeve proximal end 142, a pressure mechanism 150 having a pressure mechanism distal end 151 and a pressure mechanism proximal end 152, and a piston 160 having a piston distal end 161 and a piston proximal end 162. Illustratively, handle base component 110 may comprise a handle base interface 115 configured to interface with handle base 120, e.g., at handle base proximal end 122. Handle base component 110, handle base 120, inner sleeve 130, protective sleeve 140, pressure mechanism 150, and piston 160 may be manufactured from any suitable material, e.g., polymers, metals, metal alloys, etc., or from any combination of suitable materials.

Figure 2B:
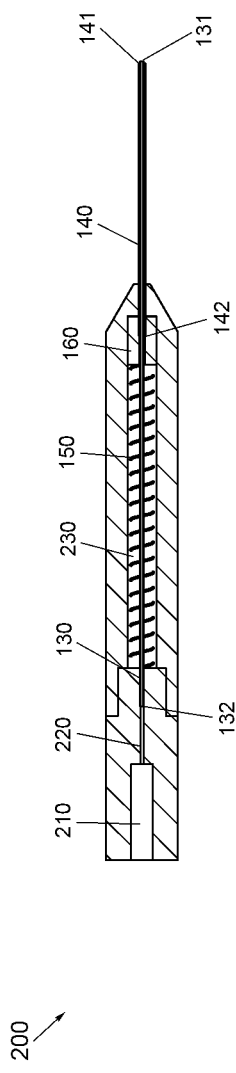
FIGS. 2A and 2B are schematic diagrams illustrating a surgical instrument.
Figure 2A:
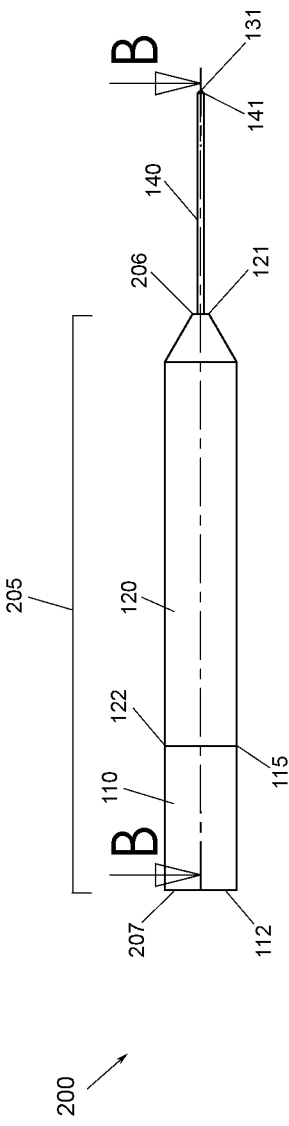

FIGS. 2A and 2B are schematic diagrams illustrating a surgical instrument 200. FIG. 2A illustrates a top view of a surgical instrument 200. In one or more embodiments, a surgical instrument 200 may comprise a handle 205 having a handle distal end 206 and a handle proximal end 207. Illustratively, handle distal end 206 may comprise handle base distal end 121. In one or more embodiments, handle proximal end 207 may comprise handle base component proximal end 112. FIG. 2B illustrates a cross-sectional view of a surgical instrument 200. Illustratively, surgical instrument 200 may comprise a proximal chamber 210, a lumen 220, and a distal chamber 230. In one or more embodiments, a portion of protective sleeve 140 may be disposed within piston 160, e.g., protective sleeve proximal end 142 may be disposed within piston 160. Illustratively, a portion of protective sleeve 140 may be fixed to piston 160, e.g., protective sleeve proximal end 142 may be fixed to piston distal end 161. In one or more embodiments, protective sleeve 140 may be fixed to piston 160, e.g., by an adhesive or any other suitable fixation means. Illustratively, a portion of protective sleeve 140 may be fixed within an inner portion of piston 160, e.g., protective sleeve proximal end 142 may be fixed to an inner portion of piston 160. In one or more embodiments, protective sleeve 140 may be fixed within an inner portion of piston 160, e.g., by an adhesive or any other suitable fixation means.

Illustratively, a portion of inner sleeve 130 may be fixed to a portion of handle base component 110, e.g., inner sleeve proximal end 132 may be fixed to handle base component distal end 111. In one or more embodiments, inner sleeve 130 may be fixed to handle base component 110, e.g., by an adhesive or any other suitable fixation means. Illustratively, a portion of inner sleeve 130 may be disposed within handle base component 110, e.g., inner sleeve proximal end 132 may be disposed within lumen 220. In one or more embodiments, inner sleeve 130 may be fixed to an inner portion of handle base component 110, e.g., inner sleeve proximal end 132 may be fixed within lumen 220. Illustratively, inner sleeve 130 may be fixed to an inner portion of handle base component 110, e.g., by an adhesive or by any other suitable fixation means.

In one or more embodiments, handle base component 110 may be fixed to handle base 120, e.g., handle base interface 115 may be fixed to handle base proximal end 122. Illustratively, handle base component 110 may be fixed to handle base 120, e.g., by an adhesive or any other suitable fixation means. In one or more embodiments, inner sleeve 130 may be disposed within lumen 220, distal chamber 230, piston 160, and protective sleeve 140. Illustratively, distal chamber 230 may comprise an inner bore of handle 205. In one or more embodiments, a portion of distal chamber 230 may be coated with a lubricant, e.g., Teflon. Illustratively, pressure mechanism 150 may be disposed within distal chamber 230. In one or more embodiments, piston 160 may be disposed within distal chamber 230. Illustratively, pressure mechanism 150 may be disposed between piston 160 and handle base component 110, e.g., pressure mechanism proximal end 152 may abut handle base component distal end 111 and pressure mechanism distal end 151 may abut piston proximal end 162.

In one or more embodiments, pressure mechanism 150 may be configured to provide a force. Illustratively, pressure mechanism 150 may be configured to provide a constant or uniform force. In one or more embodiments, pressure mechanism 150 may be configured to provide a variable force. Illustratively, pressure mechanism 150 may comprise a spring or a coil. In one or more embodiments, pressure mechanism 150 may comprise a spring having a spring constant in a range of 0.001 N/mm to 5.0 N/mm. Illustratively, pressure mechanism 150 may comprise a spring having a spring constant less than 0.001 N/mm or greater than 5.0 N/mm. In one or more embodiments, pressure mechanism 150 may comprise a pneumatic system. Illustratively, pressure mechanism 150 may be configured to provide a resistive force to resist an actuation of piston 160 within distal chamber 230, e.g., an actuation of piston 160 towards handle proximal end 207 and away from handle distal end 206. In one or more embodiments, pressure mechanism 150 may be configured to provide a facilitating force to facilitate an actuation of piston 160 within distal chamber 230, e.g., an actuation of piston 160 towards handle distal end 206 and away from handle proximal end 207.

In one or more embodiments, pressure mechanism 150 may be configured to provide a force, e.g., to piston proximal end 162. Illustratively, an application of a force to protective sleeve 140, e.g., applied to protective sleeve distal end 141, may be configured to actuate piston 160 within distal chamber 230, e.g., towards handle proximal end 207 and away from handle distal end 206. In one or more embodiments, an application of a force to protective sleeve distal end 141, e.g., a force having a magnitude greater than a force provided by pressure mechanism 150 to piston proximal end 162, may be configured to actuate piston 160 within distal chamber 230, e.g., towards handle proximal end 207 and away from handle distal end 206. Illustratively, an actuation of piston 160 within distal chamber 230, e.g., towards handle proximal end 207 and away from handle distal end 206, may be configured to retract protective sleeve 140 relative to inner sleeve 130. In one or more embodiments, a retraction of protective sleeve 140 relative to inner sleeve 130 may be configured to gradually expose a portion of inner sleeve 130. Illustratively, pressure mechanism 150 may be configured to provide a force, e.g., a force to piston proximal end 162, configured to resist an actuation of piston 160 within distal chamber 230, e.g., towards handle proximal end 207 and away from handle distal end 206.

In one or more embodiments, pressure mechanism 150 may be configured to provide a force, e.g., to piston proximal end 162. Illustratively, a reduction of a force applied to protective sleeve 140, e.g., a force applied to protective sleeve distal end 141, may be configured to actuate piston 160 within distal chamber 230, e.g., towards handle distal end 206 and away from handle proximal end 207. In one or more embodiments, a reduction of a force applied to protective sleeve distal end 141, e.g., a reduction of a force having a magnitude greater than a force provided by pressure mechanism 150 to piston proximal end 162, may be configured to actuate piston 160 within distal chamber 230, e.g., towards handle distal end 206 and away from handle proximal end 207. Illustratively, an actuation of piston 160 within distal chamber 230, e.g., towards handle distal end 206 and away from handle proximal end 207, may be configured to extend protective sleeve 140 relative to inner sleeve 130. In one or more embodiments, an extension of protective sleeve 140 relative to inner sleeve 130 may be configured to gradually enclose a portion of inner sleeve 130 within protective sleeve 140. Illustratively, pressure mechanism 150 may be configured to provide a force, e.g., a force to piston proximal end 162, configured to facilitate an actuation of piston 160 within distal chamber 230, e.g., towards handle distal end 206 and away from handle proximal end 207.

Figure 3A:
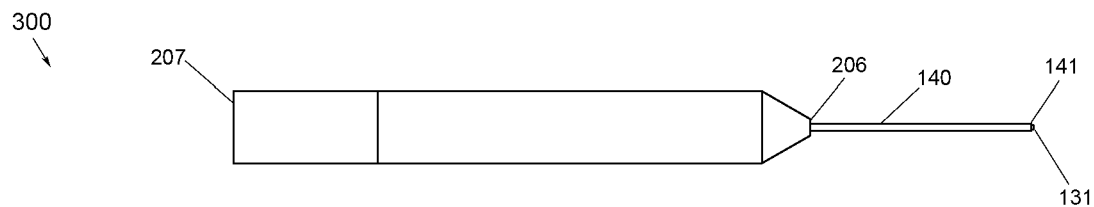
FIGS. 3A, 3B, 3C, and 3D are schematic diagrams illustrating a retraction of protective sleeve.

FIGS. 3A, 3B, 3C, and 3D are schematic diagrams illustrating a retraction of protective sleeve 140. FIG. 3A illustrates a protective sleeve in a fully extended position 300. In one or more embodiments, protective sleeve 140 may comprise a protective sleeve in a fully extended position 300, e.g., when piston 160 is fully extended within distal chamber 230. Illustratively, protective sleeve 140 may be configured to protect inner sleeve 130, e.g., when protective sleeve 140 comprises a protective sleeve in a fully extended position 300.

Figure 3B:
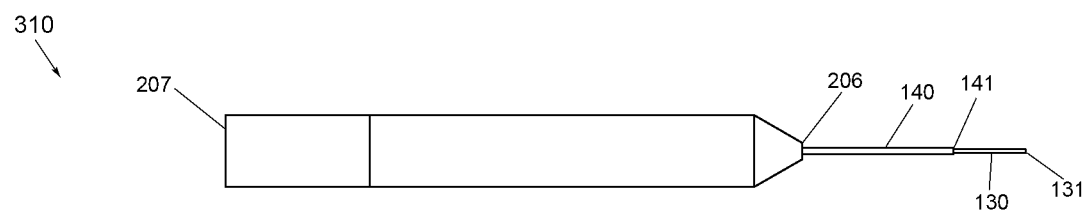

FIG. 3B illustrates a protective sleeve in a first retracted position 310. In one or more embodiments, an application of a force to protective sleeve distal end 141 may be configured to retract protective sleeve 140 relative to inner sleeve 130. Illustratively, an application of a force to protective sleeve distal end 141 may be configured to retract protective sleeve 140 from a protective sleeve in a fully extended position 300 to a protective sleeve in a first retracted position 310. In one or more embodiments, a retraction of protective sleeve 140 relative to inner sleeve 130 may be configured to expose a portion of inner sleeve 130, e.g., inner sleeve distal end 131. Illustratively, a retraction of protective sleeve 140 relative to inner sleeve 130 may be configured to retract piston 160 within distal chamber 230, e.g., actuate piston 160 within distal chamber 230 towards handle proximal end 207 and away from handle distal end 206. In one or more embodiments, a retraction of piston 160 within distal chamber 230 may be configured to retract a portion of protective sleeve 140 into distal chamber 230, e.g., protective sleeve proximal end 142. Illustratively, pressure mechanism 150 may be configured to provide a resistive force to resist a retraction of piston 160 within distal chamber 230. In one or more embodiments, protective sleeve distal end 141 may be retracted a first distance from inner sleeve distal end 131, e.g., when protective sleeve 140 comprises a protective sleeve in a first retracted position 310.

Figure 3C:
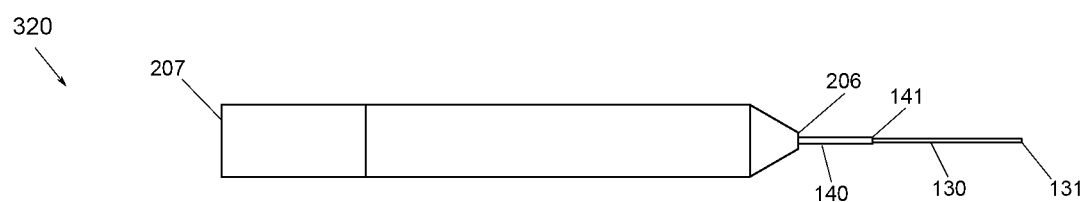

FIG. 3C illustrates a protective sleeve in a second retracted position 320. In one or more embodiments, an application of a force to protective sleeve distal end 141 may be configured to retract protective sleeve 140 relative to inner sleeve 130. Illustratively, an application of a force to protective sleeve distal end 141 may be configured to retract protective sleeve 140 from a protective sleeve in a first refracted position 310 to a protective sleeve in a second retracted position 320. In one or more embodiments, a retraction of protective sleeve 140 relative to inner sleeve 130 may be configured to expose a portion of inner sleeve 130. Illustratively, a retraction of protective sleeve 140 relative to inner sleeve 130 may be configured to retract piston 160 within distal chamber 230, e.g., actuate piston 160 within distal chamber 230 towards handle proximal end 207 and away from handle distal end 206. In one or more embodiments, a retraction of piston 160 within distal chamber 230 may be configured to retract a portion of protective sleeve 140 into distal chamber 230. Illustratively, pressure mechanism 150 may be configured to provide a resistive force to resist a retraction of piston 160 within distal chamber 230. In one or more embodiments, protective sleeve distal end 141 may be retracted a second distance from inner sleeve distal end 131, e.g., when protective sleeve 140 comprises a protective sleeve in a second retracted position 320. Illustratively, the second distance from inner sleeve distal end 131 may be any distance greater than the first distance from inner sleeve distal end 131.

Figure 3D:
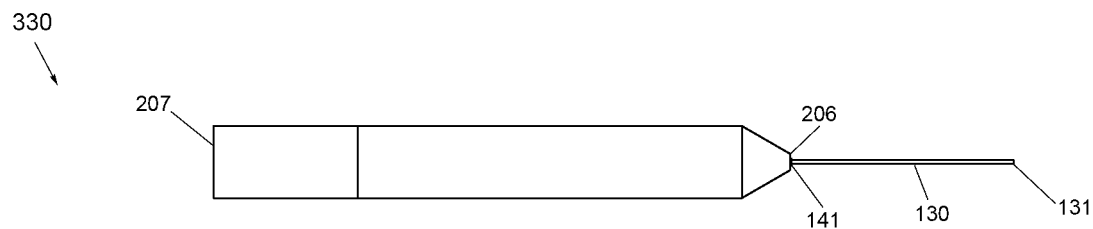

FIG. 3D illustrates a protective sleeve in a third retracted position 330. In one or more embodiments, an application of a force to protective sleeve distal end 141 may be configured to retract protective sleeve 140 relative to inner sleeve 130. Illustratively, an application of a force to protective sleeve distal end 141 may be configured to retract protective sleeve 140 from a protective sleeve in a second retracted position 320 to a protective sleeve in a third retracted position 330. In one or more embodiments, a retraction of protective sleeve 140 relative to inner sleeve 130 may be configured to expose a portion of inner sleeve 130. Illustratively, a retraction of protective sleeve 140 relative to inner sleeve 130 may be configured to retract piston 160 within distal chamber 230, e.g., actuate piston 160 within distal chamber 230 towards handle proximal end 207 and away from handle distal end 206. In one or more embodiments, a retraction of piston 160 within distal chamber 230 may be configured to retract a portion of protective sleeve 140 into distal chamber 230. Illustratively, pressure mechanism 150 may be configured to provide a resistive force to resist a retraction of piston 160 within distal chamber 230. In one or more embodiments, protective sleeve distal end 141 may be refracted a third distance from inner sleeve distal end 131, e.g., when protective sleeve 140 comprises a protective sleeve in a third retracted position 330. Illustratively, the third distance from inner sleeve distal end 131 may be any distance greater than the second distance from inner sleeve distal end 131.

Figure 4A:
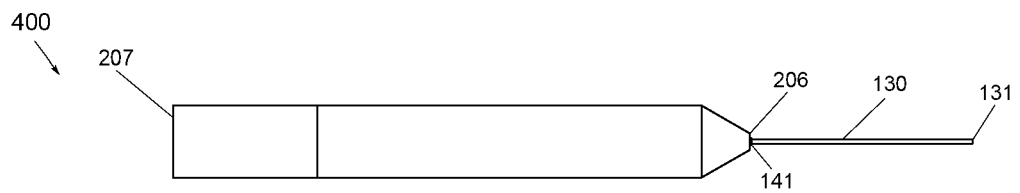
FIGS. 4A, 4B, 4C, and 4D are schematic diagrams illustrating an extension of protective sleeve.

FIGS. 4A, 4B, 4C, and 4D are schematic diagrams illustrating an extension of protective sleeve 140. FIG. 4A illustrates a protective sleeve in a fully retracted position 400. In one or more embodiments, protective sleeve 140 may comprise a protective sleeve in a fully retracted position 400, e.g., when piston 160 is fully retracted within distal chamber 230. Illustratively, protective sleeve 140 may be configured to expose inner sleeve 130, e.g., when protective sleeve 140 comprises a protective sleeve in a fully retracted position 400.

Figure 4B:
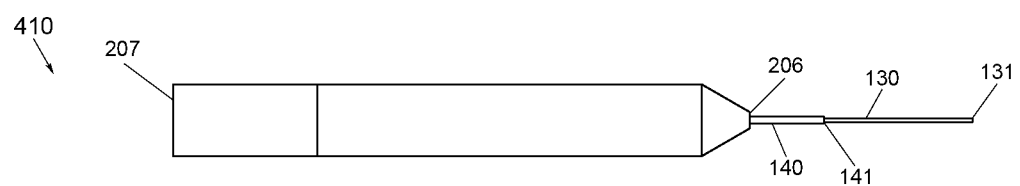

FIG. 4B illustrates a protective sleeve in a first extended position 410. In one or more embodiments, a reduction of a force applied to protective sleeve distal end 141 may be configured to extend protective sleeve 140 relative to inner sleeve 130. Illustratively, a reduction of a force applied to protective sleeve distal end 141 may be configured to extend protective sleeve 140 from a protective sleeve in a fully retracted position 400 to a protective sleeve in a first extended position 410. In one or more embodiments, an extension of protective sleeve 140 relative to inner sleeve 130 may be configured to cover a portion of inner sleeve 130, e.g., an exposed portion of inner sleeve 130. Illustratively, an extension of protective sleeve 140 relative to inner sleeve 130 may be configured to extend piston 160 within distal chamber 230, e.g., actuate piston 160 within distal chamber 230 towards handle distal end 206 and away from handle proximal end 207. In one or more embodiments, an extension of piston 160 within distal chamber 230 may be configured to extend a portion of protective sleeve 140 out from distal chamber 230, e.g., protective sleeve distal end 141. Illustratively, pressure mechanism 150 may be configured to provide a facilitating force to facilitate an extension of piston 160 within distal chamber 230. In one or more embodiments, protective sleeve distal end 141 may be extended a first extended distance from handle distal end 206, e.g., when protective sleeve 140 comprises a protective sleeve in a first extended position 410.

Figure 4C:
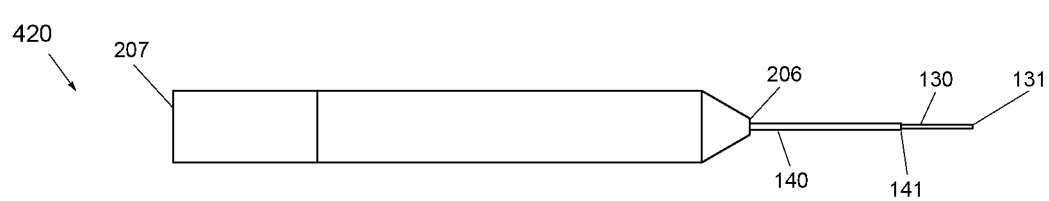

FIG. 4C illustrates a protective sleeve in a second extended position 420. In one or more embodiments, a reduction of a force applied to protective sleeve distal end 141 may be configured to extend protective sleeve 140 relative to inner sleeve 130. Illustratively, a reduction of a force applied to protective sleeve distal end 141 may be configured to extend protective sleeve 140 from a protective sleeve in a first extended position 410 to a protective sleeve in a second extended position 420. In one or more embodiments, an extension of protective sleeve 140 relative to inner sleeve 130 may be configured to cover a portion of inner sleeve 130, e.g., an exposed portion of inner sleeve 130. Illustratively, an extension of protective sleeve 140 relative to inner sleeve 130 may be configured to extend piston 160 within distal chamber 230, e.g., actuate piston 160 within distal chamber 230 towards handle distal end 206 and away from handle proximal end 207. In one or more embodiments, an extension of piston 160 within distal chamber 230 may be configured to extend a portion of protective sleeve 140 out from distal chamber 230. Illustratively, pressure mechanism 150 may be configured to provide a facilitating force to facilitate an extension of piston 160 within distal chamber 230. In one or more embodiments, protective sleeve distal end 141 may be extended a second extended distance from handle distal end 206, e.g., when protective sleeve 140 comprises a protective sleeve in a second extended position 420. Illustratively, the second extended distance from handle distal end 206 may comprise any distance greater than the first extended distance from handle distal end 206.

Figure 4D:

FIG. 4D illustrates a protective sleeve in a third extended position 430. In one or more embodiments, a reduction of a force applied to protective sleeve distal end 141 may be configured to extend protective sleeve 140 relative to inner sleeve 130. Illustratively, a reduction of a force applied to protective sleeve distal end 141 may be configured to extend protective sleeve 140 from a protective sleeve in a second extended position 420 to a protective sleeve in a third extended position 430. In one or more embodiments, an extension of protective sleeve 140 relative to inner sleeve 130 may be configured to cover a portion of inner sleeve 130, e.g., an exposed portion of inner sleeve 130. Illustratively, an extension of protective sleeve 140 relative to inner sleeve 130 may be configured to extend piston 160 within distal chamber 230, e.g., actuate piston 160 within distal chamber 230 towards handle distal end 206 and away from handle proximal end 207. In one or more embodiments, an extension of piston 160 within distal chamber 230 may be configured to extend a portion of protective sleeve 140 out from distal chamber 230. Illustratively, pressure mechanism 150 may be configured to provide a facilitating force to facilitate an extension of piston 160 within distal chamber 230. In one or more embodiments, protective sleeve distal end 141 may be extended a third extended distance from handle distal end 206, e.g., when protective sleeve 140 comprises a protective sleeve in a third extended position 430. Illustratively, the third extended distance from handle distal end 206 may comprise any distance greater than the second extended distance from handle distal end 206.

In one or more embodiments, a surgeon may insert a surgical instrument tip, e.g., inner sleeve distal end 131, into a cannula. A cannula is often used in surgical procedures having a surgical target site that is located beneath an outer layer of tissue. For example, an ophthalmic surgeon may use a cannula to perform a surgical procedure on a portion of an inner eye. Illustratively, an ophthalmic surgeon may make a small incision in an outer tissue of an eye, e.g., cornea, sclera, etc., and then the surgeon may insert a cannula into the small incision. Once the cannula is inserted into the small incision, the surgeon may utilize the cannula as a passageway to access a portion of the inner eye, e.g., a surgical target site. Illustratively, the surgeon may perform a surgical procedure by inserting a surgical instrument into the inner eye through the cannula, e.g., to perform a portion of the surgical procedure.

After performing a portion of the surgical procedure, the surgeon may remove the surgical instrument from the inner eye through the cannula.

In one or more embodiments, protective sleeve 140 may be configured to protect inner sleeve 130 as a portion of inner sleeve, e.g., inner sleeve distal end 131, is inserted into a cannula. Illustratively, inner sleeve 130 may comprise an inner sleeve diameter, a cannula may comprise a cannula diameter, and protective sleeve 140 may comprise a protective sleeve diameter. In one or more embodiments, an inner sleeve diameter may be smaller than a cannula diameter. Illustratively, a cannula diameter may be smaller than or equal to a protective sleeve diameter. In one or more embodiments, a surgeon may guide protective sleeve distal end 141 towards an end of a cannula, e.g., when protective sleeve 140 comprises a protective sleeve in a fully extended position 300. Illustratively, the surgeon may insert inner sleeve distal end 131 into the cannula and gradually extend inner sleeve 130 through the cannula, e.g., to perform a portion of a surgical procedure. In one or more embodiments, as inner sleeve 130 is gradually inserted into a cannula, protective sleeve 140 may be gradually extended over the cannula. Illustratively, as protective sleeve 140 is gradually extended over a cannula, protective sleeve distal end 141 may contact a barrier, e.g., a cannula flange, configured to prevent protective sleeve 140 from further extension over the cannula. In one or more embodiments, a surgeon may guide inner sleeve 130 further into a cannula, e.g., to a surgical target site, after protective sleeve distal end 141 contacts a barrier. Illustratively, a further insertion of inner sleeve 130 into a cannula after protective sleeve distal end 141 has contacted a barrier may be configured to retract protective sleeve 140 relative to inner sleeve 130. In one or more embodiments, a further insertion of inner sleeve 130 into a cannula after protective sleeve distal end 141 has contacted a barrier may be configured to retract protective sleeve 140 from a protective sleeve in a fully extended position 300 to a protective sleeve in a first refracted position 310.

Illustratively, protective sleeve 140 may be configured to protect inner sleeve 130 as inner sleeve 130 is removed from a cannula, e.g., after a surgeon performs a portion of a surgical procedure. In one or more embodiments, a surgeon may start to retract a portion of inner sleeve 130 out from a cannula, e.g., when protective sleeve 140 comprises a protective sleeve in a fully retracted position 400. Illustratively, a retraction of inner sleeve 130 out from a cannula may be configured to reduce a force applied to protective sleeve distal end 141. In one or more embodiments, a reduction of a force applied to protective sleeve distal end 141 may be configured to extend protective sleeve 140 relative to inner sleeve 130. Illustratively, a reduction of a force applied to protective sleeve distal end 141 may be configured to extend protective sleeve 140 from a protective sleeve in a fully retracted position 400 to a protective sleeve in a first extended position 410. In one or more embodiments, an extension of protective sleeve 140 relative to inner sleeve 130 may be configured to extend protective sleeve 140 over a portion of inner sleeve 130, e.g., a portion of inner sleeve 130 retracted out from a cannula.

Illustratively, one or more properties of a surgical instrument may be adjusted to attain one or more desired surgical instrument features. In one or more embodiments, a surgical instrument may be manufactured without pressure mechanism 150. Illustratively, pressure mechanism 150 may be disposed within distal chamber 230 wherein pressure mechanism proximal end 152 may abut piston distal end 161. In one or more embodiments, pressure mechanism 150 may be configured to provide a resistive force configured to resist an extension of protective sleeve 140 relative to inner sleeve 130.

Illustratively, pressure mechanism 150 may be configured to provide a facilitating force configured to facilitate a retraction of protective sleeve 140 relative to inner sleeve 130.

For example, protective sleeve 140 may be configured to retract relative to inner sleeve 130, e.g., to expose inner sleeve distal end 131 for a surgical procedure. Illustratively, protective sleeve 140 may be configured to retract relative to inner sleeve 130, e.g., but protective sleeve 140 may not be configured to extend relative to inner sleeve 130. For example, protective sleeve 140 may be configured to extend relative to inner sleeve 130, e.g., to enclose inner sleeve distal end 131 within protective sleeve 140 after a surgical procedure. In one or more embodiments, protective sleeve 140 may be configured to extend relative to inner sleeve 130, e.g., but protective sleeve 140 may not be configured to retract relative to inner sleeve 130.

Illustratively, a switch or a lever may be added to manipulate a retraction or an extension of protective sleeve 140 relative to inner sleeve 130. In one or more embodiments, either an actuation of a switch or an application of a force to protective sleeve distal end 141 may be configured to retract protective sleeve 140 relative to inner sleeve 130. Illustratively, either an actuation of a lever or an application of a force to protective sleeve distal end 141 may be configured to retract protective sleeve 140 relative to inner sleeve 130. In one or more embodiments, either an actuation of a switch or a reduction of a force applied to protective sleeve distal end 141 may be configured to extend protective sleeve 140 relative to inner sleeve 130. Illustratively, either an actuation of a lever or a reduction of a force applied to protective sleeve distal end 141 may be configured to extend protective sleeve 140 relative to inner sleeve 130. In one or more embodiments, either an actuation of a switch or an actuation of a lever may be configured to retract protective sleeve 140 relative to inner sleeve 130. Illustratively, either an actuation of a switch or an actuation of a lever may be configured to extend protective sleeve 140 relative to inner sleeve 130.

In one or more embodiments, inner sleeve 130 may be configured to house a surgical instrument tip. Illustratively, inner sleeve 130 may comprise a surgical instrument tip. In one or more embodiments, a retraction of protective sleeve 140 relative to inner sleeve 130 may be configured to expose a surgical instrument tip, e.g., before a surgeon performs a surgical procedure. Illustratively, an extension of protective sleeve 140 relative to inner sleeve 130 may be configured to protect a surgical instrument tip, e.g., before or after a surgeon performs a surgical procedure. In one or more embodiments, one or more properties of pressure mechanism 150 may be adjusted, e.g., to vary an amount of force applied to protective sleeve distal end 141 configured to retract protective sleeve 140 relative to inner sleeve 130. Illustratively, a spring constant of pressure mechanism 150 may be adjusted to vary an amount of force applied to protective sleeve distal end 141 configured to retract protective sleeve 140 relative to inner sleeve 130.

Figure 5:
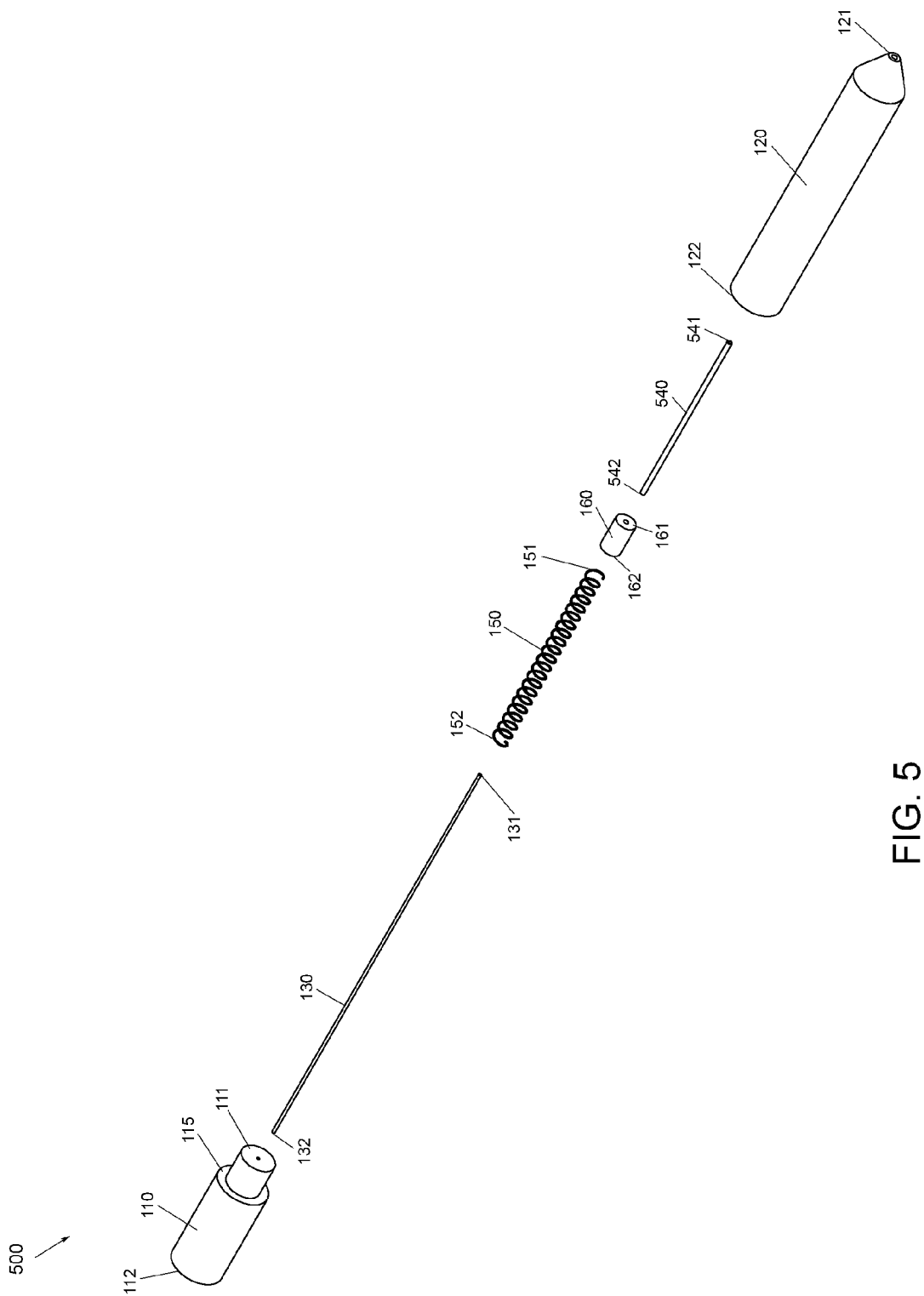
FIG. 5 is a schematic diagram illustrating an exploded view of a surgical instrument assembly.

FIG. 5 is a schematic diagram illustrating an exploded view of a surgical instrument assembly 500. In one or more embodiments, a surgical instrument assembly 500 may comprise a handle base component 110 having a handle base component distal end 111 and a handle base component proximal end 112, a handle base 120 having a handle base distal end 121 and a handle base proximal end 122, an inner sleeve 130 having an inner sleeve distal end 131 and an inner sleeve proximal end 132, a support sleeve 540 having a support sleeve distal end 541 and a support sleeve proximal end 542, a pressure mechanism 150 having a pressure mechanism distal end 151 and a pressure mechanism proximal end 152, and a piston 160 having a piston distal end 161 and a piston proximal end 162. Illustratively, handle base component 110 may comprise a handle base interface 115 configured to interface with handle base 120, e.g., at handle base proximal end 122. Handle base component 110, handle base 120, inner sleeve 130, support sleeve 540, pressure mechanism 150, and piston 160 may be manufactured from any suitable material, e.g., polymers, metals, metal alloys, etc., or from any combination of suitable materials.

Illustratively, support sleeve 540 may be configured to increase a stiffness of inner sleeve 130. In one or more embodiments, inner sleeve 130 may have a first stiffness and support sleeve 540 may have a second stiffness. Illustratively, the second stiffness may be greater than the first stiffness. In one or more embodiments, a portion of support sleeve 540 may be configured to decrease a flexibility of a portion of inner sleeve 130 by enclosing the portion of inner sleeve 130 within the portion of support sleeve 540. Illustratively, a portion of support sleeve 540 may be configured to prevent inner sleeve 130 from bending or flexing, e.g., during a surgical procedure. In one or more embodiments, a portion of support sleeve 540 may be configured to cause inner sleeve distal end 131 to actuate in a predictable manner, e.g., during a surgical procedure.

FIGS. 6A and 6B are schematic diagrams illustrating a surgical instrument 600. FIG. 6A illustrates a top view of a surgical instrument 600. In one or more embodiments, a surgical instrument 600 may comprise a handle 205 having a handle distal end 206 and a handle proximal end 207. Illustratively, handle distal end 206 may comprise handle base distal end 121. In one or more embodiments, handle proximal end 207 may comprise handle base component proximal end 112. FIG. 6B illustrates a cross-sectional view of a surgical instrument 600. Illustratively, surgical instrument 600 may comprise a proximal chamber 210, a lumen 220, and a distal chamber 230. In one or more embodiments, a portion of support sleeve 540 may be disposed within piston 160, e.g., support sleeve proximal end 542 may be disposed within piston 160. Illustratively, a portion of support sleeve 540 may be fixed to piston 160, e.g., support sleeve proximal end 542 may be fixed to piston distal end 161.

In one or more embodiments, support sleeve 540 may be fixed to piston 160, e.g., by an adhesive or any other suitable fixation means. Illustratively, a portion of support sleeve 540 may be fixed within an inner portion of piston 160, e.g., support sleeve proximal end 542 may be fixed to an inner portion of piston 160. In one or more embodiments, support sleeve 540 may be fixed within an inner portion of piston 160, e.g., by an adhesive or any other suitable fixation means. Illustratively, a portion of inner sleeve 130 may be fixed to a portion of handle base component 110, e.g., inner sleeve proximal end 132 may be fixed to handle base component distal end 111. In one or more embodiments, inner sleeve 130 may be fixed to handle base component 110, e.g., by an adhesive or any other suitable fixation means. Illustratively, a portion of inner sleeve 130 may be disposed within handle base component 110, e.g., inner sleeve proximal end 132 may be disposed within lumen 220. In one or more embodiments, inner sleeve 130 may be fixed to an inner portion of handle base component 110, e.g., inner sleeve proximal end 132 may be fixed within lumen 220. Illustratively, inner sleeve 130 may be fixed to an inner portion of handle base component 110, e.g., by an adhesive or by any other suitable fixation means.

In one or more embodiments, handle base component 110 may be fixed to handle base 120, e.g., handle base interface 115 may be fixed to handle base proximal end 122. Illustratively, handle base component 110 may be fixed to handle base 120, e.g., by an adhesive or any other suitable fixation means. In one or more embodiments, inner sleeve 130 may be disposed within lumen 220, distal chamber 230, piston 160, and support sleeve 540. Illustratively, distal chamber 230 may comprise an inner bore of handle 205. In one or more embodiments, a portion of distal chamber 230 may be coated with a lubricant, e.g., Teflon. Illustratively, pressure mechanism 150 may be disposed within distal chamber 230. In one or more embodiments, piston 160 may be disposed within distal chamber 230. Illustratively, pressure mechanism 150 may be disposed between piston 160 and handle base component 110, e.g., pressure mechanism proximal end 152 may abut handle base component distal end 111 and pressure mechanism distal end 151 may abut piston proximal end 162.

In one or more embodiments, pressure mechanism 150 may be configured to provide a force. Illustratively, pressure mechanism 150 may be configured to provide a constant or uniform force. In one or more embodiments, pressure mechanism 150 may be configured to provide a variable force. Illustratively, pressure mechanism 150 may comprise a spring or a coil. In one or more embodiments, pressure mechanism 150 may comprise a spring having a spring constant in a range of 0.001 N/mm to 5.0 N/mm. Illustratively, pressure mechanism 150 may comprise a spring having a spring constant less than 0.001 N/mm or greater than 5.0 N/mm. In one or more embodiments, pressure mechanism 150 may comprise a pneumatic system. Illustratively, pressure mechanism 150 may be configured to provide a resistive force to resist an actuation of piston 160 within distal chamber 230, e.g., an actuation of piston 160 towards handle proximal end 207 and away from handle distal end 206. In one or more embodiments, pressure mechanism 150 may be configured to provide a facilitating force to facilitate an actuation of piston 160 within distal chamber 230, e.g., an actuation of piston 160 towards handle distal end 206 and away from handle proximal end 207.

In one or more embodiments, pressure mechanism 150 may be configured to provide a force, e.g., to piston proximal end 162. Illustratively, an application of a force to support sleeve 540, e.g., applied to support sleeve distal end 541, may be configured to actuate piston 160 within distal chamber 230, e.g., towards handle proximal end 207 and away from handle distal end 206. In one or more embodiments, an application of a force to support sleeve distal end 541, e.g., a force having a magnitude greater than a force provided by pressure mechanism 150 to piston proximal end 162, may be configured to actuate piston 160 within distal chamber 230, e.g., towards handle proximal end 207 and away from handle distal end 206. Illustratively, an actuation of piston 160 within distal chamber 230, e.g., towards handle proximal end 207 and away from handle distal end 206, may be configured to retract support sleeve 540 relative to inner sleeve 130. In one or more embodiments, a retraction of support sleeve 540 relative to inner sleeve 130 may be configured to gradually expose a portion of inner sleeve 130. Illustratively, pressure mechanism 150 may be configured to provide a force, e.g., a force to piston proximal end 162, configured to resist an actuation of piston 160 within distal chamber 230, e.g., towards handle proximal end 207 and away from handle distal end 206.

In one or more embodiments, pressure mechanism 150 may be configured to provide a force, e.g., to piston proximal end 162. Illustratively, a reduction of a force applied to support sleeve 540, e.g., a force applied to support sleeve distal end 541, may be configured to actuate piston 160 within distal chamber 230, e.g., towards handle distal end 206 and away from handle proximal end 207. In one or more embodiments, a reduction of a force applied to support sleeve distal end 541, e.g., a reduction of a force having a magnitude greater than a force provided by pressure mechanism 150 to piston proximal end 162, may be configured to actuate piston 160 within distal chamber 230, e.g., towards handle distal end 206 and away from handle proximal end 207. Illustratively, an actuation of piston 160 within distal chamber 230, e.g., towards handle distal end 206 and away from handle proximal end 207, may be configured to extend support sleeve 540 relative to inner sleeve 130. In one or more embodiments, an extension of support sleeve 540 relative to inner sleeve 130 may be configured to gradually enclose a portion of inner sleeve 130 within support sleeve 540. Illustratively, pressure mechanism 150 may be configured to provide a force, e.g., a force to piston proximal end 162, configured to facilitate an actuation of piston 160 within distal chamber 230, e.g., towards handle distal end 206 and away from handle proximal end 207.

Figure 7B:
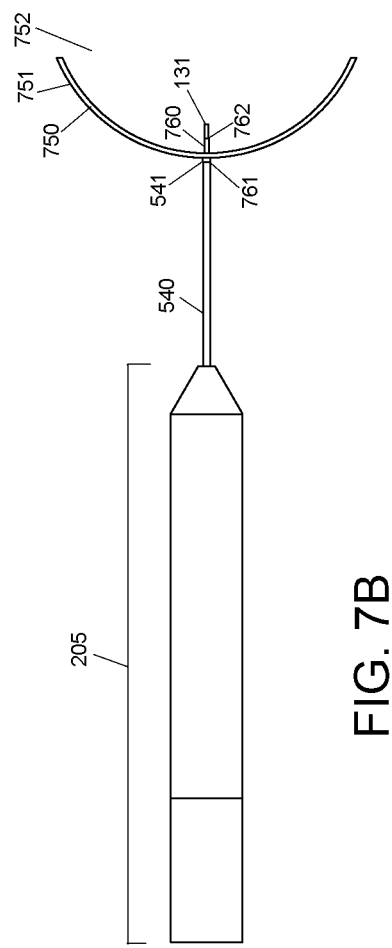

FIGS. 7A, 7B, 7C, 7D, and 7E are schematic diagrams illustrating a surgical procedure with a surgical instrument 600. FIG. 7A illustrates a surgical instrument in a first surgical position 700. In one or more embodiments, a surgical instrument 600 may comprise a surgical instrument in a first surgical position 700 when support sleeve 540 is fully extended relative to inner sleeve 130. Illustratively, a surgical instrument 600 may comprise a surgical instrument in a first surgical position 700 when support sleeve distal end 541 is aligned with a cannula 760 inserted in an eye 750. In one or more embodiments, cannula 760 may comprise a support sleeve interface 761 and a cannula end 762. An ophthalmologic surgeon may insert cannula 760 into an incision in corneal or scleral tissue 751 of eye 750, e.g., in order to access a surgical target site within inner eye 752. After cannula 760 is inserted into eye 750, the ophthalmologic surgeon may access inner eye 752 via cannula 760 without causing excessive trauma to corneal or scleral tissue 751.

FIG. 7B illustrates a surgical instrument in a second surgical position 710. In one or more embodiments, a surgical instrument 600 may comprise a surgical instrument in a second surgical position 710 when support sleeve 540 is partially retracted relative to inner sleeve 130. Illustratively, a surgical instrument 600 may comprise a surgical instrument in a second surgical position 710 when support sleeve distal end 541 is interfaced with support sleeve interface 761. In one or more embodiments, a surgeon may guide a surgical instrument 600 from a surgical instrument in a first position 700 to a surgical instrument in a second position 710 by advancing support sleeve distal end 541 towards support sleeve interface 761 until support sleeve distal end 541 contacts support sleeve interface 761, and then guiding inner sleeve distal end 131 through cannula 760, e.g., and into inner eye 752. Illustratively, when support sleeve distal end 541 is interfaced with support sleeve interface 761, the surgeon may guide inner sleeve 130 through cannula 760 by advancing handle distal end 206 towards cannula 760.

In one or more embodiments, a diameter of inner sleeve 130 may be less than a diameter of cannula 760. Illustratively, a diameter of support sleeve 540 may be greater than or equal to a diameter of cannula 760. In one or more embodiments, inner sleeve 130 may be manufactured with dimensions configured to allow inner sleeve 130 to be inserted through cannula 760. Illustratively, support sleeve 540 may be manufactured with dimensions configured to prevent support sleeve 540 from being inserted through cannula 760. In one or more embodiments, advancing handle distal end 206 towards cannula 760 after support sleeve distal end 541 has contacted support sleeve interface 761 may be configured to apply a force to support sleeve distal end 541. Illustratively, an application of a force to support sleeve distal end 541 may be configured to retract support sleeve 540 relative to inner sleeve. In one or more embodiments, as inner sleeve 130 is gradually advanced through cannula 760, support sleeve 540 may be gradually retracted into handle 205, e.g., into distal chamber 230. Illustratively, pressure mechanism 150 may be configured to provide a resistive force to resist a retraction of support sleeve 540 relative to inner sleeve 130.

Figure 7C:
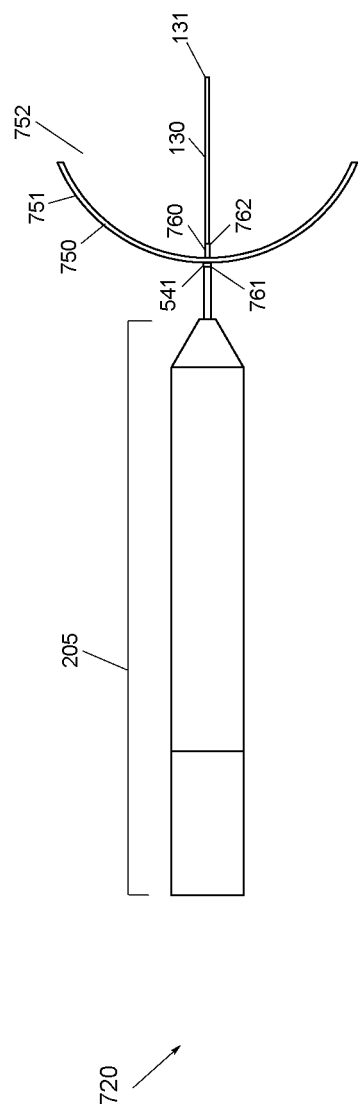

FIG. 7C illustrates a surgical instrument in a third surgical position 720. Illustratively, a surgical instrument 600 may comprise a surgical instrument in a third surgical position 720 when support sleeve 540 is partially retracted relative to inner sleeve 130. In one or more embodiments, a surgical instrument 600 may comprise a surgical instrument in a third surgical position 720 when a surgeon has advanced inner sleeve distal end 131 a particular distance within inner eye 752, e.g., the particular distance within inner eye 752 may be associated with a surgical target site location. Illustratively, a surgeon may guide a surgical instrument 600 from a surgical instrument in a second position 710 to a surgical instrument in a third position 720 by advancing handle distal end 206 towards cannula 760. In one or more embodiments, advancing handle distal end 206 towards cannula 760 may be configured to retract support sleeve 540 relative to inner sleeve 130. Illustratively, pressure mechanism 150 may be configured to provide a resistive force to resist a retraction of support sleeve 540 relative to inner sleeve 130.

In one or more embodiments, a portion of support sleeve 540 may be configured to enclose a portion of inner sleeve 130, e.g., to increase a stiffness of a portion of inner sleeve 130. Illustratively, a portion of support sleeve 540 may be configured to enclose a portion of inner sleeve 130, e.g., to decrease a flexibility of a portion of inner sleeve 130. In one or more embodiments, a surgeon may attempt to adjust a position of inner sleeve 130 within inner eye 752, e.g., by adjusting a position of handle 205. Illustratively, a portion of support sleeve 540 may be configured to prevent inner sleeve 130 from actuating unexpectedly within inner eye 752, e.g., in response to an adjustment of a position of handle 205. In one or more embodiments, a portion of support sleeve 540 may be configured to prevent inner sleeve 130 from bending or flexing, e.g., in response to an adjustment of a position of handle 205.

Figure 7D:
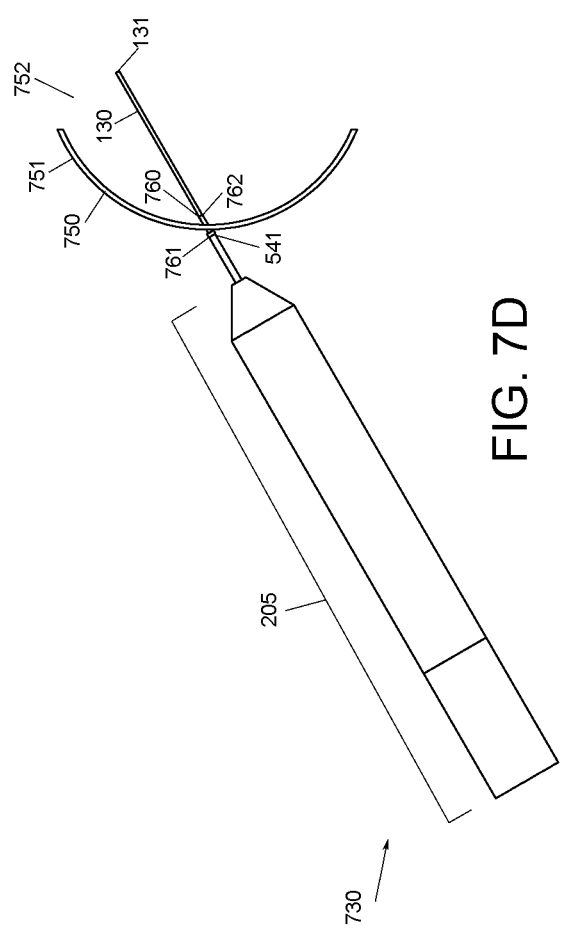

FIG. 7D illustrates a surgical instrument adjusted to access a surgical site in a superior portion of an inner eye 730. In one or more embodiments, a surgeon may actuate a surgical instrument 600 from a surgical instrument in a third surgical position 720 to a surgical instrument adjusted to access a surgical site in a superior portion of an inner eye 730 by adjusting a position of handle 205, e.g., by actuating handle 205 within a sagittal plane of eye 750. Illustratively, a surgeon may actuate a surgical instrument from a surgical instrument in a third surgical position 720 to a surgical instrument adjusted to access a surgical site in a superior portion of an inner eye 730 by actuating handle 205 within a sagittal plane of eye 750 in a counter-clockwise direction. In one or more embodiments, an actuation of handle 205 within a sagittal plane of eye 750 in a counter-clockwise direction may actuate inner sleeve 130 within the sagittal plane of eye 750 in a counter-clockwise direction.

Illustratively, a portion of support sleeve 540 may be configured to enclose a portion of inner sleeve 130, e.g., to increase a stiffness of a portion of inner sleeve 130. In one or more embodiments, a portion of support sleeve 540 may be configured to enclose a portion of inner sleeve 130, e.g., to decrease a flexibility of a portion of inner sleeve 130. Illustratively, a portion of support sleeve 540 may be configured to prevent inner sleeve 130 from actuating unexpectedly within inner eye 752, e.g., in response to an actuation of handle 205 within a sagittal plane of eye 750 in a counter-clockwise direction. In one or more embodiments, a portion of support sleeve 540 may be configured to prevent inner sleeve 130 from actuating within a sagittal plane of eye 750 in a clockwise direction, e.g., in response to an actuation of handle 205 within the sagittal plane of eye 750 in a counter-clockwise direction. Illustratively, a portion of support sleeve 540 may be configured to prevent inner sleeve 130 from bending or flexing, e.g., in response to an actuation of handle 205 within a sagittal plane of eye 750 in a counter-clockwise direction. In one or more embodiments, a portion of support sleeve 540 may be configured to cause inner sleeve 130 to actuate within a sagittal plane of eye 750 in a counter-clockwise direction, e.g., in response to an actuation of handle 205 within the sagittal plane of eye 750 in a counter-clockwise direction.

Figure 7E:
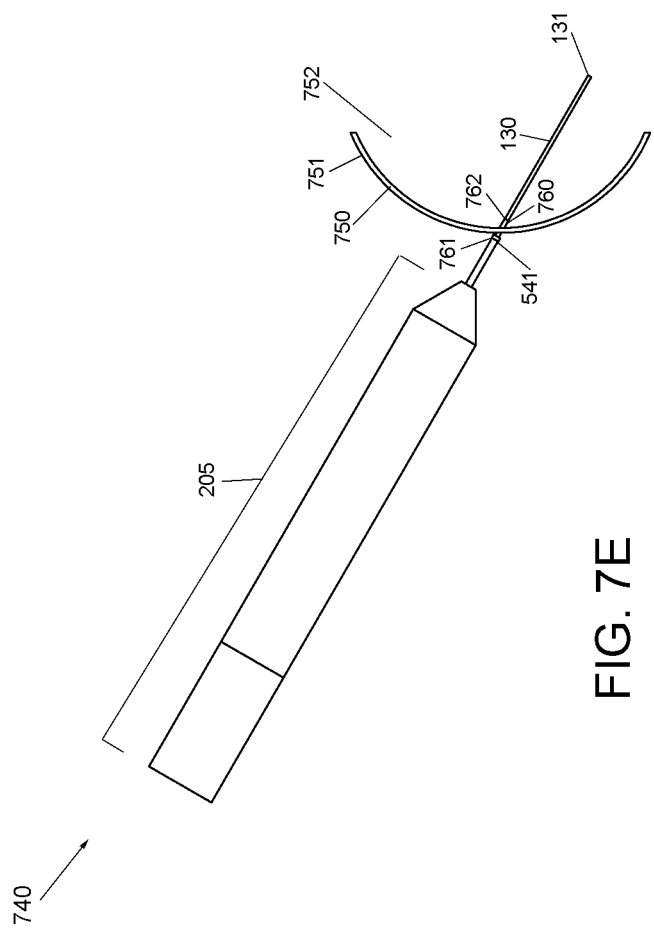

FIG. 7E illustrates a surgical instrument adjusted to access a surgical site in an inferior portion of an inner eye 740. In one or more embodiments, a surgeon may actuate a surgical instrument 600 from a surgical instrument in a third surgical position 720 to a surgical instrument adjusted to access a surgical site in an inferior portion of an inner eye 740 by adjusting a position of handle 205, e.g., by actuating handle 205 within a sagittal plane of eye 750. Illustratively, a surgeon may actuate a surgical instrument from a surgical instrument in a third surgical position 720 to a surgical instrument adjusted to access a surgical site in an inferior portion of an inner eye 740 by actuating handle 205 within a sagittal plane of eye 750 in a clockwise direction. In one or more embodiments, an actuation of handle 205 within a sagittal plane of eye 750 in a clockwise direction may actuate inner sleeve 130 within the sagittal plane of eye 750 in a clockwise direction.

Illustratively, a portion of support sleeve 540 may be configured to extend over a portion of inner sleeve 130, e.g., to increase a stiffness of a portion of inner sleeve 130. In one or more embodiments, a portion of support sleeve 540 may be configured to extend over a portion of inner sleeve 130, e.g., to decrease a flexibility of a portion of inner sleeve 130. Illustratively, a portion of support sleeve 540 may be configured to prevent inner sleeve 130 from actuating unexpectedly within inner eye 752, e.g., in response to an actuation of handle 205 within a sagittal plane of eye 750 in a clockwise direction. In one or more embodiments, a portion of support sleeve 540 may be configured to prevent inner sleeve 130 from actuating within a sagittal plane of eye 750 in a counter-clockwise direction, e.g., in response to an actuation of handle 205 within the sagittal plane of eye 750 in a clockwise direction. Illustratively, a portion of support sleeve 540 may be configured to prevent inner sleeve 130 from bending, e.g., in response to an actuation of handle 205 within a sagittal plane of eye 750 in a clockwise direction. In one or more embodiments, a portion of support sleeve 540 may be configured to cause inner sleeve 130 to actuate within a sagittal plane of eye 750 in a clockwise direction, e.g., in response to an actuation of handle 205 within the sagittal plane of eye 750 in a clockwise direction.

In one or more embodiments, one or more properties of a surgical instrument may be adjusted to attain one or more surgical instrument features. Illustratively, support sleeve 540 may be replaced with a wire configured to increase a stiffness of a portion of inner sleeve 130. In one or more embodiments, a surgical instrument may not comprise a support sleeve 540. For example, a portion of inner sleeve 130 may be manufactured with a material configured to increase a stiffness of the portion of inner sleeve 130. Illustratively, a portion of inner sleeve 130 may be manufactured with dimensions configured to increase a stiffness of the portion of inner sleeve 130. In one or more embodiments, a surgical instrument may comprise multiple layers of sleeves. Illustratively, a protective sleeve 140 may be disposed over support sleeve 540, and support sleeve 540 may be disposed over inner sleeve 130. In one or more embodiments, protective sleeve 140 may be configured to protect support sleeve 540 and inner sleeve 130 from damage before or after a surgical procedure.

Illustratively, pressure mechanism 150 may be configured to minimize a force applied to eye 750 during a surgical procedure. In one or more embodiments, pressure mechanism 150 may comprise a spring having a spring constant in a range of 0.0001 N/m to 100 N/m, e.g., to minimize a force applied to eye 750 during a surgical procedure. Illustratively, pressure mechanism 150 may comprise a spring having a spring constant below 0.0001 N/m or above 100 N/m, e.g., to minimize a force applied to eye 750 during a surgical procedure. In one or more embodiments, support sleeve 540 may be configured to minimize a force applied to eye 750 during a surgical procedure. Illustratively, a geometry of support sleeve 540 may be configured to dissipate a force, e.g., a force provided by pressure mechanism 150, to minimize a force applied to eye 750 during a surgical procedure. For example, support sleeve 540 may be manufactured with a diamond or a triangle mesh pattern to dissipate a force provided by pressure mechanism 150, e.g., to minimize a force applied to eye 750.

In one or more embodiments, support sleeve distal end 541 may be configured to minimize a force applied to eye 750 during a surgical procedure, e.g., by dissipating a force provided by pressure mechanism 150. Illustratively, support sleeve distal end 541 may comprise a cushion material or a padding material configured to dissipate a force provided by pressure mechanism 150, e.g., to minimize a force applied to eye 750 during a surgical procedure. In one or more embodiments, a surface area of support sleeve distal end 541 may be increased to transfer a force provided by pressure mechanism 150 over a larger area of eye 750, e.g., to minimize a risk of trauma to eye 750. Illustratively, a surface area of support sleeve distal end 541 may be decreased to transfer a force provided by pressure mechanism 150 over a smaller area of eye 750, e.g., to minimize an area of eye 750 exposed to a force provided by pressure mechanism 150.

In one or more embodiments, one or more properties of a surgical instrument may be configured to minimize an increase in intraocular pressure ("IOP") during a surgical procedure. The medically accepted normal range of IOP is between 10 mmHg and 20 mmHg. Normal IOP may increase or decrease approximately 3 mmHg as a result of normal conditions. Illustratively, pressure mechanism 150 may be configured to provide a force having a magnitude configured to increase IOP by less than 3 mmHg during a surgical procedure. In one or more embodiments, support sleeve 540 may be configured to dissipate a force provided by pressure mechanism 150 wherein the dissipated force is configured to increase IOP by less than 3 mmHg during a surgical procedure.

Illustratively, a surgical instrument may be configured to both protect inner sleeve 130 from damage before or after a surgical procedure and to increase a stiffness of a portion of inner sleeve 130, e.g., to prevent inner sleeve 130 from actuating in an unexpected manner when inserted in a cannula. In one or more embodiments, protective sleeve 140 may be configured with the functionality of support sleeve 540. Illustratively, support sleeve 540 may be configured with the functionality of protective sleeve 140. Accordingly, support sleeve 540 and protective sleeve 140 may be considered as interchangeable in any one or more embodiments.

The foregoing description has been directed to particular embodiments of this invention. It will be apparent; however, that other variations and modifications may be made to the described embodiments, with the attainment of some or all of their advantages. Specifically, it should be noted that the principles of the present invention may be implemented in any instrument. Furthermore, while this description has been written in terms of a surgical instrument, the teachings of the present invention are equally suitable to systems where the functionality of any embodiment may be employed. Therefore, it is the object of the appended claims to cover all such variations and modifications as come within the true spirit and scope of the invention.

What is claimed is:

1. An instrument comprising:
   a handle having a handle distal end and a handle proximal end;
   a handle base of the handle having a handle base distal end and a handle base proximal end;
   a handle base component of the handle having a handle base component distal end, a handle base component proximal end, and a handle base interface, the handle base interface disposed between the handle base component distal end and the handle base component proximal end, the handle base component partially disposed within the handle base wherein the handle base proximal end is fixed to the handle base interface and wherein the handle base distal end is the handle distal end and the handle base component proximal end is the handle proximal end;
   a piston having a piston distal end and a piston proximal end, the piston distal end and the piston proximal end disposed within an inner bore of the handle wherein the inner bore is disposed between the handle base component distal end and the handle distal end;
   an inner sleeve having an inner sleeve distal end and an inner sleeve proximal end wherein the inner sleeve proximal end is completely disposed within a lumen of the handle base component, the inner sleeve having a first stiffness;
   a support sleeve having a support sleeve distal end and a support sleeve proximal end wherein the support sleeve proximal end is fixed within the piston, the support sleeve having a second stiffness wherein the second stiffness is greater than the first stiffness and wherein a portion of the support sleeve is configured to decrease a flexibility of a portion of the inner sleeve; and
   a protected portion of the inner sleeve, the protected portion of the inner sleeve disposed within the piston and the support sleeve.

2. The instrument of claim 1 further comprising:
   a pressure mechanism configured to provide a force, the pressure mechanism disposed within the inner bore of the handle.

3. The instrument of claim 2 wherein the support sleeve is configured to retract relative to the inner sleeve.

4. The instrument of claim 3 wherein a retraction of the support sleeve relative to the inner sleeve is configured to expose a portion of the protected portion of the inner sleeve.

5. The instrument of claim 4 wherein the force provided by the pressure mechanism resists the retraction of the support sleeve relative to the inner sleeve.

6. The instrument of claim 2 wherein the support sleeve is configured to extend relative to the inner sleeve.

7. The instrument of claim 6 wherein an extension of the support sleeve relative to the inner sleeve is configured to protect an exposed portion of the inner sleeve.

8. The instrument of claim 7 wherein the force provided by the pressure mechanism facilitates the extension of the support sleeve relative to the inner sleeve.

9. The instrument of claim 2 further comprising: an ophthalmic cannula having an ophthalmic cannula diameter and a proximal end; a support sleeve diameter of the support sleeve; an inner sleeve diameter of the inner sleeve; wherein the inner sleeve diameter is smaller than the ophthalmic cannula diameter; the cannula comprises of a support sleeve interface at the proximal end and the interface allows the inner sleeve to extend through the cannula.

10. The instrument of claim 9 wherein the support sleeve diameter is greater than the ophthalmic cannula diameter.

11. The instrument of Claim 10 where in an insertion of the inner sleeve into the ophthalmic cannula retracts the support sleeve relative to the inner sleeve.

12. The instrument of claim 11 wherein the insertion of the inner sleeve into the ophthalmic cannula retracts the support sleeve into the handle.

13. The instrument of claim 10 wherein a retraction of the inner sleeve out of the ophthalmic cannula extends the support sleeve relative to the inner sleeve.

14. The instrument of claim 13 wherein the retraction of the inner sleeve out of the ophthalmic cannula extends the support sleeve out from the handle.

15. The instrument of claim 2 wherein the pressure mechanism comprises a spring.

16. The instrument of claim 15 further comprising:
a spring constant of the spring, the spring constant within a spring constant range of 0.001 N/mm to 5.0 N/mm.

17. An instrument comprising:
a handle having a handle distal end and a handle proximal end;
a handle base of the handle having a handle base distal end and a handle base proximal end;
a handle base component of the handle having a handle base component distal end, a handle base component proximal end, and a handle base interface, the handle base interface disposed between the handle base component distal end and the handle base component proximal end, the handle base component partially disposed within the handle base wherein the handle base proximal end is fixed to the handle base interface and wherein the handle base distal end is the handle distal end and the handle base component proximal end is the handle proximal end;
a piston having a piston distal end and a piston proximal end, the piston distal end and the piston proximal end disposed within an inner bore of the handle wherein the inner bore is disposed between the handle base component distal end and the handle distal end;
an inner sleeve having an inner sleeve distal end and an inner sleeve proximal end wherein the inner sleeve proximal end is completely disposed within a lumen of the handle base component, the inner sleeve having an inner sleeve diameter less than a diameter of an ophthalmic cannula;
a support sleeve having a support sleeve distal end and a support sleeve proximal end wherein the support sleeve proximal end is fixed within the piston, the support sleeve having a support sleeve diameter greater than the diameter of the ophthalmic cannula; and
a protected portion of the inner sleeve, the protected portion of the inner sleeve disposed within the piston and the support sleeve wherein the support sleeve is configured to reduce a flexibility of the protected portion of the inner sleeve.

18. An instrument comprising:
a handle having a handle distal end and a handle proximal end;
a handle base of the handle having a handle base distal end and a handle base proximal end;
a handle base component of the handle having a handle base component distal end, a handle base component proximal end, and a handle base interface, the handle base interface disposed between the handle base component distal end and the handle base component proximal end, the handle base component partially disposed within the handle base wherein the handle base proximal end is fixed to the handle base interface and wherein the handle base distal end is the handle distal end and the handle base component proximal end is the handle proximal end;
a piston having a piston distal end and a piston proximal end, the piston distal end and the piston proximal end disposed within an inner bore of the handle wherein the inner bore is disposed between the handle base component distal end and the handle distal end;
an inner sleeve having an inner sleeve distal end and an inner sleeve proximal end wherein the inner sleeve proximal end is completely disposed within a lumen of the handle base component, the inner sleeve having a first stiffness;
an inner sleeve diameter of the inner sleeve, the inner sleeve diameter less than a diameter of an ophthalmic cannula;
a support sleeve having a support sleeve distal end and a support sleeve proximal end wherein the support sleeve proximal end is fixed within the piston, the support sleeve having a second stiffness wherein the second stiffness is greater than the first stiffness;
a support sleeve diameter of the support sleeve, the support sleeve diameter greater than the diameter of the ophthalmic cannula; and
a protected portion of the inner sleeve, the protected portion of the inner sleeve disposed within the piston and the support sleeve.

* * * * *